(12) United States Patent
Chien et al.

(10) Patent No.: US 9,402,664 B2
(45) Date of Patent: Aug. 2, 2016

(54) DYNAMIC INTRAMEDULLARY HARDWARE

(71) Applicants: Karen Chien, Chicago, IL (US); Khara Quiney, Chicago, IL (US); Evan Boetticher, Cupertino, CA (US)

(72) Inventors: Karen Chien, Chicago, IL (US); Khara Quiney, Chicago, IL (US); Evan Boetticher, Cupertino, CA (US)

(73) Assignee: Torjo Medical Solutions, Inc., Dover, DE (US)

( * ) Notice: Subject to any disclaimer, the term of this patent is extended or adjusted under 35 U.S.C. 154(b) by 0 days.

(21) Appl. No.: 14/085,822

(22) Filed: Nov. 21, 2013

(65) Prior Publication Data

US 2014/0081268 A1   Mar. 20, 2014

Related U.S. Application Data

(63) Continuation of application No. 13/043,173, filed on Mar. 8, 2011, now Pat. No. 8,617,160.

(60) Provisional application No. 61/311,873, filed on Mar. 9, 2010.

(51) Int. Cl.
*A61B 17/72* (2006.01)

(52) U.S. Cl.
CPC .................................. *A61B 17/7266* (2013.01)

(58) Field of Classification Search
CPC ..................................................... A61B 17/7266
USPC ............. 606/62–68, 304, 313, 323, 326, 327
See application file for complete search history.

(56) References Cited

U.S. PATENT DOCUMENTS

| | | | |
|---|---|---|---|
| 3,779,239 A | 12/1973 | Fischer |
| 3,986,504 A | 10/1976 | Avila |
| 4,204,531 A | 5/1980 | Aginsky |
| 4,227,518 A | 10/1980 | Aginsky |
| 4,237,875 A | 12/1980 | Termanini |
| 4,275,717 A | 6/1981 | Bolesky |
| 4,453,539 A | 6/1984 | Raftopoulos et al. |
| 4,519,100 A | 5/1985 | Wills et al. |
| 4,721,103 A | 1/1988 | Freedland |
| 4,854,312 A | 8/1989 | Raftopoulos et al. |
| 4,862,883 A | 9/1989 | Freeland |
| 5,057,103 A | 10/1991 | Davis |
| 5,578,035 A | 11/1996 | Lin |
| 6,077,265 A | 6/2000 | Werding et al. |
| 6,443,954 B1 | 9/2002 | Bramlet et al. |
| 6,447,513 B1 | 9/2002 | Griggs |
| 6,524,313 B1 | 2/2003 | Fassier |
| 6,558,388 B1 | 5/2003 | Bartsch et al. |
| 6,575,973 B1 | 6/2003 | Shekalim |
| 6,736,818 B2 | 5/2004 | Perren |
| 6,780,185 B2 | 8/2004 | Frei |
| 7,029,476 B2 | 4/2006 | Hansson |
| 7,097,648 B1 | 8/2006 | Globerman et al. |
| 7,601,152 B2 | 10/2009 | Levy et al. |
| 7,846,162 B2 | 12/2010 | Nelson et al. |

*Primary Examiner* — Pedro Philogene
*Assistant Examiner* — David C Comstock
(74) *Attorney, Agent, or Firm* — Evan Boetticher

(57) ABSTRACT

An intramedullary nail comprising an outer tubular sheath, a flexible rod and a driver element mobile within the sheath longitudinally with an engagement element formed out of the wall of the tubular sheath. After the nail has been inserted, distal end first, into the intramedullary cavity, the flexible rod is pulled, thereby engendering the driver element to advance the engagement element into the cortical bone, thus keeping the intramedullary nail in position within the intramedullary cavity.

19 Claims, 4 Drawing Sheets

DYNAMIC INTRAMEDULLARY HARDWARE

RELATIONSHIP TO PRIOR APPLICATION

This application is a continuation of application Ser. No. 13/043,173 filed Mar. 8, 2011 which claims priority from the U.S. Provisional Patent Application No. 61/311,873 filed Mar. 9, 2010, both of which are incorporated herein by reference.

FIELD OF THE INVENTION

The present invention relates to an intermedullary device for the stabilization of osseous matter for the purpose of improved healing and mobility during healing.

BACKGROUND

Typically, an intramedullary nail is placed into the intramedullary cavity of physically compromised osseous material in order to maintain proper alignment of the material for optimal healing. The intramedullary nail is then secured by screws to allow support of the bone so that the patient can use the appendage during healing. Previous intramedullary nails had holes on both the distal and proximal ends for the insertion of fixtures, such as screws, that go through the intramedullary hardware and compromised osseous material. The holes that are closest to the point of nail insertion are called the "proximal" holes and those furthest away are the "distal" holes. The most commonly used system for securing an intramedullary nail uses an external guide or jig to find the proximal holes in the nail. With the assistance of the external guide or jig, the surgeon then drills through all of the tissue surrounding the bone and into the bone. For minimal damage and maximal healing, the fixture holes that are drilled into the leg and the bone must precisely align with the insertion holes in the intramedullary hardware so that the hardware can be secured with respect to the medullary canal.

Various types of external guides and jigs have been proposed to assist in the insertion of intramedullary hardware, such as shown in U.S. Pat. No. 4,733,654 A1 to Marino and U.S. Pat. No. 5,776,194 A1 to Mikol et al. Such external guides and jigs may be temporarily attached to the proximal end of the intramedullary nail to help align the bone fixtures and/or the drill to the receiving opening in the intramedullary nail. While such external guides and jigs are helpful to achieve proper alignment, their accuracy decreases they proceed from the proximal end to the distal end of the intramedullary nail. Additional solutions are needed, especially for attaching the distal end of the intramedullary nail to a distal osseous material fragment.

There are currently no effective external systems for finding the distal holes of an intramedullary nail. As mentioned above, guides for the distal hole become less reliable as distance from the proximal end of the intramedullary nail increases, particularly if any bending of the intramedullary nail has occurred. A commonly used procedure involves repeated x-raying of the patient to find the hole and then drilling through the leg into the bone. Another method for securing the distal end of the intramedullary nail is to drill the receiving opening into the intramedullary nail only after the intramedullary nail is placed into the bone, as disclosed in U.S. Pat. No. 5,057,110 A1 to Kranz et al. Bioresorbable materials, however, are not as strong as metals, leading to an intramedullary nail that is weaker than desired and has a weaker attachment than desired.

Continuing, additional problems occur with intramedullary nails using bioresorbable materials due to the healing requirements of a bone with respect to the strength and rigidity of the intramedullary nail. U.S. Pat. No. 4,756,307 A1 to Crowninshield and U.S. Pat. No. 4,338,926 A1 to Kummer et al. disclose an intramedullary nail with bioresorbable portions to weaken the nail relative to the bone over time. These intramedullary nails, however, forsake the use of a transverse bone fastener to achieve the benefit of the bioresorbable portions.

Finally, while most intramedullary nails remain in the patient's leg throughout their lifetime, the nail does occasionally need to be removed due to complications. The complications usually arise from the presence of the screws holding the nail in place. When the removal of the nail is necessary the physician must repeat the insertion procedure to find the location of the screws and drill into the leg again.

It would thus be advantageous to provide an intramedullary nail and related portions and/or components that overcomes the above-noted shortcomings.

SUMMARY OF THE INVENTION

The proposed invention solves the difficulty of the labor and time intensive process of securing an intramedullary nail within the intramedullary cavity of a bone by external screwing and drilling. The proposed invention engenders an anchoring mechanism located within the intramedullary nail to engage the cortical bone. In this way, the labor and time requirements related to securing an intramedullary nail within the intramedullary cavity are substantially reduced. Additionally, the invention achieves the advantage of reduced radiological exposure to patients and medical personnel, and reduced scarring for the patient. Use of the proposed invention is not limited to fractures of the length of the long bone, but could also be used in fractures of the ball from the rest of the long bone or for smaller bones.

Exemplary embodiments are provided, these embodiments are not to be interpreted as limitations upon the invention. In one embodiment, the bone-securing device comprises a intramedullary nail, open on both ends, having at least one or more engaging elements. The intramedullary nail may be inserted into the intramedullary cavity of a bone such that the intramedullary nail is secured within the intramedullary cavity on one or both sides of a fracture, thereby aligning the fractured bone fragments, thus allowing the promotion of healing and the formation of a new center portion from and between the splintered parts.

The invention also relates more particularly to engaging elements that are attached to the wall of intramedullary nail. The engaging elements may be attached to the intramedullary nail by, but not limited to, being cut from the material of the wall of the intramedullary nail. Attachment of the engaging elements to the nail itself allows for greater stability than prior internal anchoring devices. After the intramedullary nail is placed into the intramedullary cavity of the bone, the engaging elements are engendered to engage the surrounding cortical bone tissue. The engaging elements are preferably located at the distal end of the intramedullary nail's insertion point, but there may be a plurality of engaging elements along the length of the intramedullary nail, including at the proximal end. In some embodiments, the end of the intramedullary nail proximal to its insertion point will have openings located on its walls instead of engaging elements. These openings on the proximal end would allow for the insertion of external screws. The intramedullary nail would be compatible with an external guide to allow for the discovery of any screw holes from outside the bone.

In this invention, the engaging elements are attached to the wall of the intramedullary nail. In the preferred embodiment, the engaging elements are cut directly from the wall of the intramedullary nail so that they are integral to the intramedullary nail. In some embodiments, the materials of the intramedullary nail and that of the engaging elements are different. This may be achieved, for example, at the casting by combining the materials when the intramedullary nail is cast or they may be combined after casting, for example using a dovetail design. In the preferred embodiment, the engaging elements are curved and the tips are self-tapping to facilitate engagement with bone tissue.

The engaging elements are pushed outward by a mechanism internal to the intramedullary nail. This internal mechanism comprises a threaded flexible rod and a driver that fits within the hollow section of the intramedullary nail. The driver is located on the flexible rod and can either move along the length of the flexible rod or is secured to the flexible rod. This driver shifts position to engender the movement of the engaging elements.

In one embodiment, the internal, hollow portion of the intramedullary nail is threaded to allow for a controlled movement of the flexible rod. In this embodiment, the driver is bound to the flexible rod such that it moves upwards as the flexible rod screws upwards along the threaded portion of the intramedullary nail. The driver moves with the flexible rod longitudinally along the length of the intramedullary nail and pushes out the engaging elements as it passes through the center of the intramedullary nail.

In another embodiment, the internal flexible rod rotates in the intramedullary nail without moving longitudinally. In this embodiment, the driver is not secured in place on the rotating flexible rod, but may move along the surface of the flexible rod as the flexible rod turns. In this embodiment, the rotating flexible rod drives the driver into the space between or amongst the engaging elements. In turn, the driver pushes the engaging elements outward relative to the outer surface of the intramedullary nail. In either embodiment, the driver may remain in place between or amongst the engaging elements allowing for improved engagement properties of the engaging elements.

In another embodiment, the driver is bound to the flexible rod such that it turns with the flexible rod and is already amongst the engaging elements. The driver is shaped such that it initially allows the engaging elements to remain unengaged. Turning the flexible rod a single or partial turn engenders the driver to exert pressure on the engaging elements so that they engage the bone.

In the preferred embodiment of the invention, the distal end of the intramedullary nail is open and internally constructed to catch bone marrow as the intramedullary nail is driven into the intramedullary cavity of the bone. This internal construction involves a narrowing and curving of the inner portion of distal end such that a concave face is proffered toward any marrow entering the hollow portion of the tube. This catching of the marrow prevents the marrow from clogging any internal structures of the intramedullary nail.

In the preferred embodiment of the intramedullary nail, the intramedullary nail, the engaging elements, the flexible rod and driver(s) are independently composed of titanium alloy, cobalt chromium, stainless steel or other compounds having similar structural properties.

DETAILED DESCRIPTION OF THE INVENTION

The intramedullary nail may be placed into a long bone by cutting the outer tissue, drilling into the bone and reaming out the intramedullary space to facilitate the insertion of the intramedullary nail. A guide wire may be sent into the intramedullary space, the intramedullary nail inserted onto the guide wire, and then the intramedullary nail hammered securely into the intramedullary space so that it traverses a broken or weak point in the bone.

Figure 1:
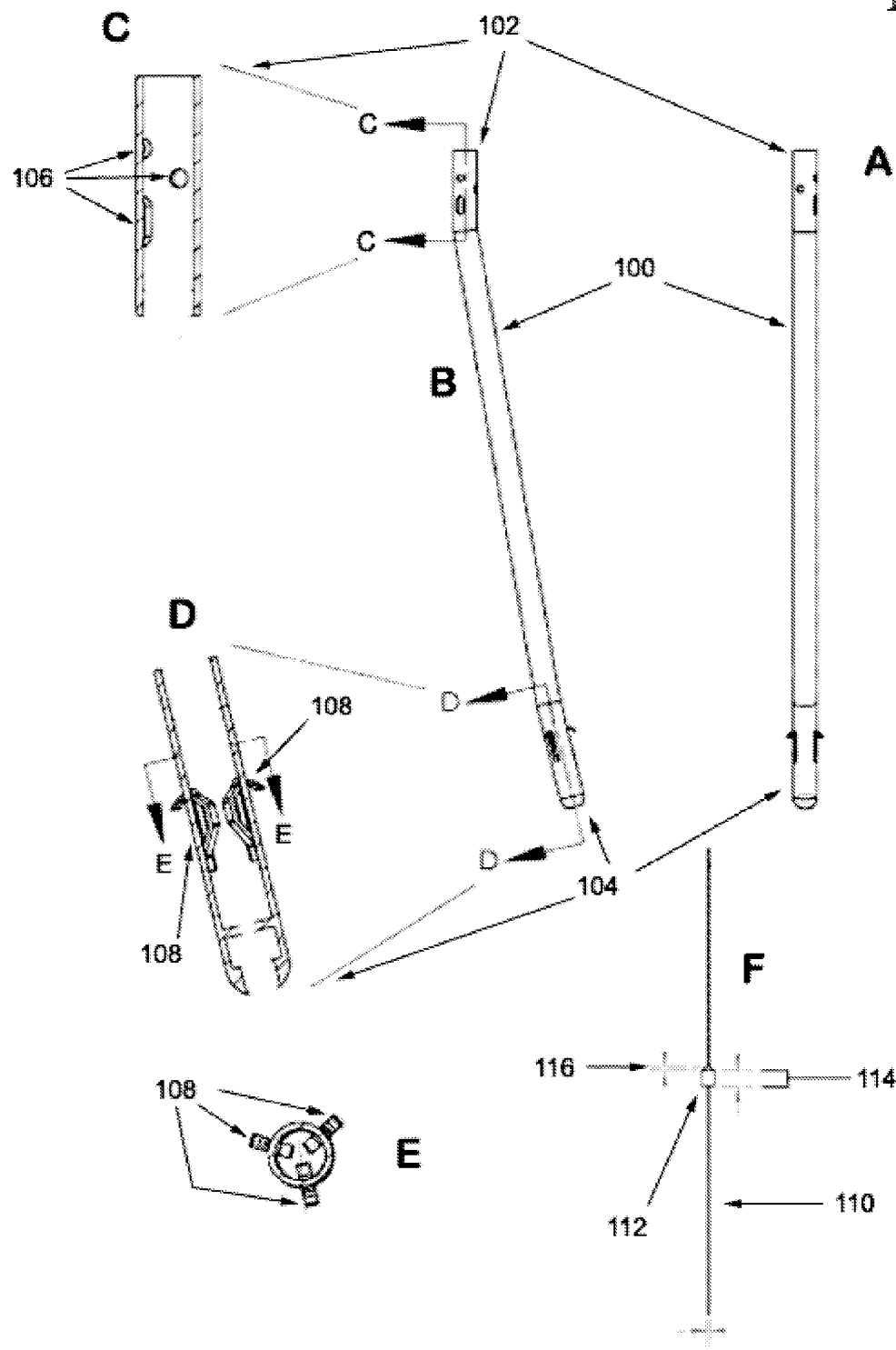
FIG. 1 is a front and side view of possible construction of the intramedullary nail with close up of the mechanism of the preferred embodiment

Referring to the FIG. 1, the intramedullary nail 100 may be bent or straight to match the structure of the intended bone. FIG. 1B is a side view of nail 100 in FIG. 1A. The nail 100 has a proximal end 102 closer to the point of insertion and a distal end 104 further from the point of insertion. The proximal end 102 may have holes 106 for the insertion of external screws (not shown) as demonstrated by FIG. 1C. The hole 106 may be circular or they may be compression holes 106. FIG. 1D shows an example of the distal end 104 wherein anchors 108 are attached to the nail. The anchors 108 may be curved as shown in FIG. 1D. The anchors 108 are able to shift position so that the tips of the anchor extend out of the nail 100 and may engage external material. FIG. 1E shows a top view cross section of the distal end 104 with the anchors 108 partially extended out of the nail 100. In the preferred embodiment, the anchors 108 are positioned fully within the nail 100 until an operator wishes to secure the distal end of the nail 100 within intramedullary space. As shown in FIG. 1D, the distal end 104 of the nail 100 may be open to allow a guide wire (not shown) to pass through the entire length of the nail 100.

The anchors 108 are able to shift position so that their tips extend out of the nail 100 and engage the surrounding cortical bone. The anchors 108 in FIG. 1D have tips that are curved toward the distal end 104, but the anchors 108 may also be attached to the nail 100 on the end of the anchor closer to the proximal end 102 of the nail 100 and the tip of the anchor 108 may be closer to the distal end 104 with the anchor 108 tip pointing toward the proximal end 102. The anchors 108 may also be perpendicular to the nail 100 so that they would appear sideways to the position of the anchors 108 shown in FIG. 1D. The anchors 108 can take a variety of shapes.

FIG. 1F shows an example of a flexible rod 110 with a driver 112 attached. The driver 112 may be attached to the flexible rod 110 in a variety of ways. For example, the driver 112 may be secured to the flexible rod 110 so that they move in unison. In another example, the flexible rod 110 may be externally threaded and the driver 112 internally threaded such that the driver 112 can screw along the flexible rod 110, thereby changing its position on the flexible rod 110. Other configurations are easily produced by a person of ordinary skill in the art. The flexible rod 110 may extend completely through the driver 112 or the driver 112 may be positioned at the terminus of the flexible rod 110. In the preferred embodiment, the flexible rod 110 is hollow to allow for the insertion of the guide wire. The driver 112 has a body 114 and a conical top 116. The driver body 114 is structured to fit within the inside of the nail 100, so that the driver 112 can move longitudinally through the nail 100.

Figure 2:
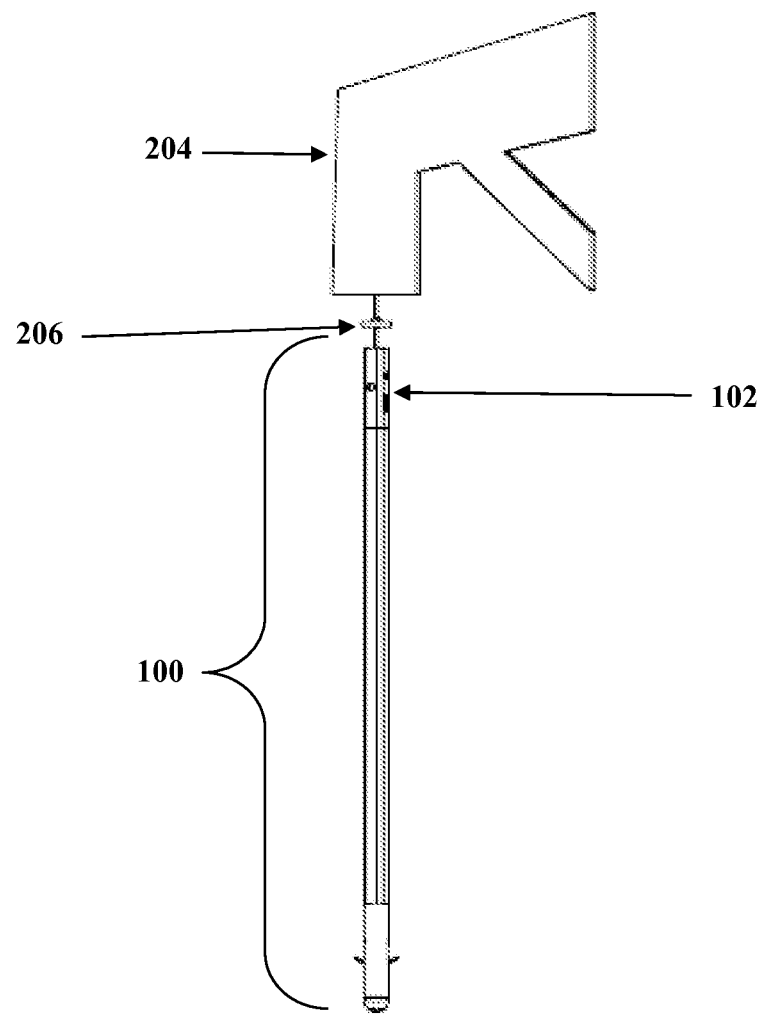
FIG. 2 is a view of a possible construction of the intramedullary nail with a handheld power device inserted and the anchors extended
Figure 3:
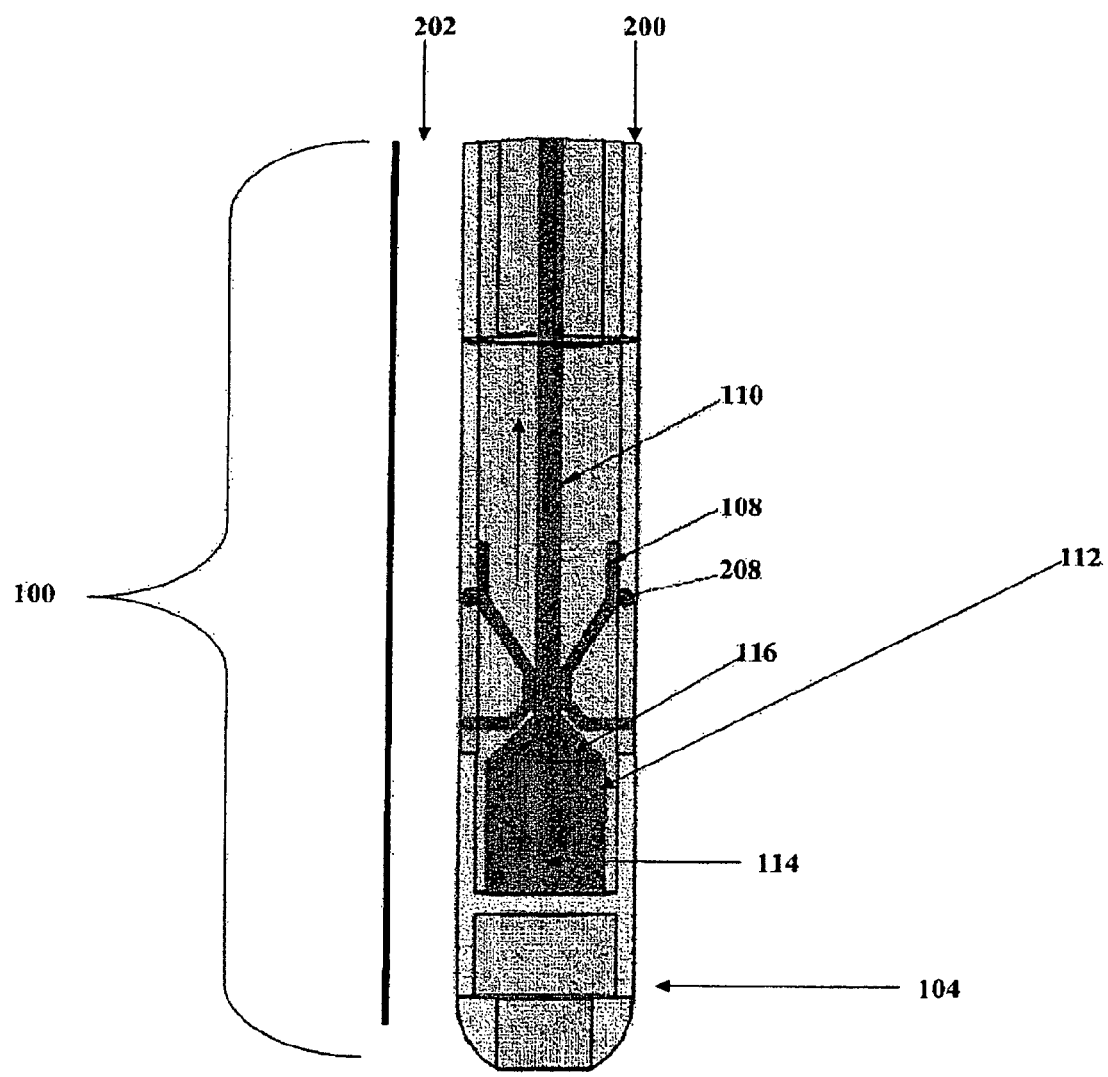
FIG. 3 is the internal structure of the intramedullary nail before the driver engages the anchors FIG. 4 the internal structure of the intramedullary nail after the driver has engaged the anchors

As demonstrated by FIG. 2, in the inventive concept, the flexible rod 110 with the attached driver 112 is positioned within the nail 100 with the conical top 116 portion closer to the anchors 108 than the driver's body 114. The driver 112 may be positioned between the anchors 108 and the proximal end 102 or the distal end 104. In the example shown in FIG. 3, the driver 112 is at the terminus of the flexible rod 110 between the anchors 108 and the distal end 104. As shown in FIG. 3, the anchors 108 are attached to the nail wall 200 and still within the nail 100 with the nail 100 pressed tightly against the intramedullary cavity wall 202. In the inventive concept, the driver 112 moves between or amongst the anchors 108 and engendered them outward to engage the bone 202. In the example shown in FIG. 2, a handheld power device 204, such as a riveting tool or similar device, may be used to pull the flexible rod 110 a particular distance toward the proximal end 102. As shown in FIG. 3, such an action will cause the driver 112 to move between or amongst the anchors 108 and push out the anchors 108 so that they engage the intramedullary cavity wall 202. As reflected in FIG. 2, so that the nail 100 is not dislodged by the force of the handheld power device 204, the nail 100 may have a brace 206 at the top to secure the handheld power device 204 in relation to the nail 100. The handheld power device 204 may also apply torque if the flexible rod 110 and driver 112 of FIG. 3 are externally and internally threaded, respectively. As displayed in FIG. 2, if the handheld power device 204 applies torque, then the brace 206 would prevent the nail 100 and the handheld power device 204 from moving respective to one another.

Figure 4:
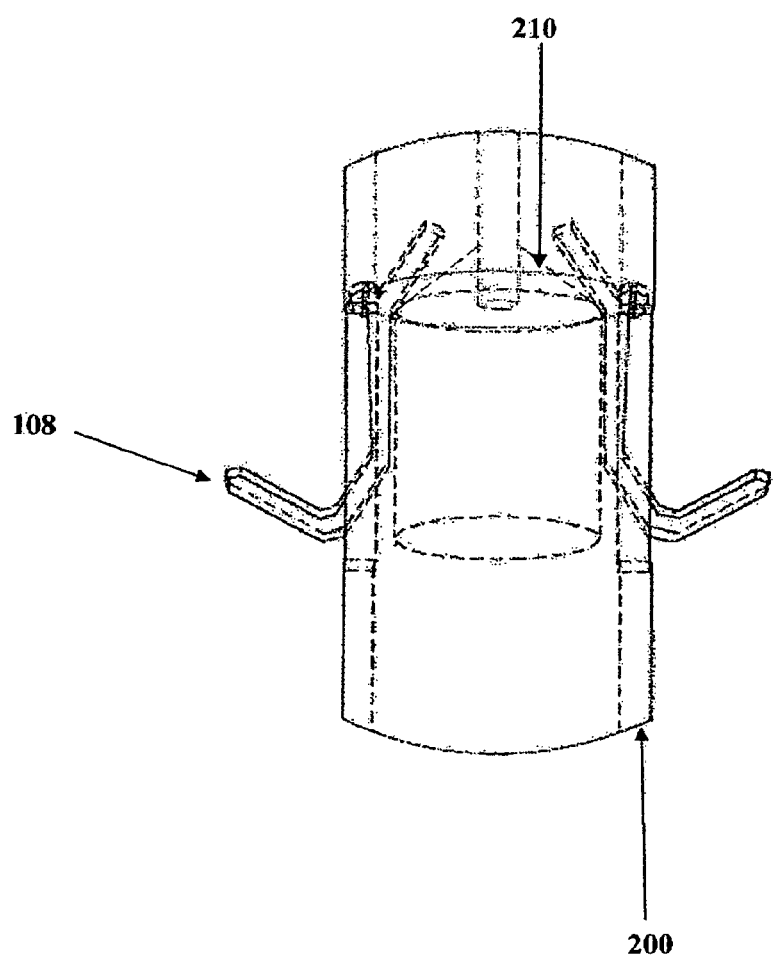

The anchors 108 may be attached to the nail wall 200 by a living hinge. The anchor 108 may also have a space 208 for the attachment of a pin (not shown) that is secured to the nail wall 200 as shown in FIG. 3. The anchors 108 may also be attached to the nail wall 200 by a wire ring 210 that is in communication with the nail wall 200 as shown in FIG. 4.

After the driver 112 has been moved a particular distance by the force applied by the handheld power device 204, the driver 112 remains between or amongst the anchors 108 to secure them in place. This creates a solid line of material through the width of the nail 100 and prevents the anchors 108 from falling back inside the nail 100.

Once the driver is in place, it can be held in place by pressure from the anchors (108) that are wedged between the driver and the intramedullary cavity wall (202). The flexible rod (110) and driver (112) may also be kept from moving through a locking mechanism. Such a locking mechanism may include a screw that goes through the flexible rod (110) or a clamp that holds the flexible rod (110) in place.

If the nail 100 needs to be removed, the handheld power device 204 is again applied and the driver 112 moves further along the length of the nail 100. The driver 112 then pushes on the internal ends of the anchors 108 and pushes them back against the inside nail wall 200. This pulls the tip of the anchor 108 out of the bone 202 so that the nail 100 may be removed.

The nail 100 may be manufactured by separately producing the proximal end 102 and the distal end 104 and joining the two ends together. In one manufacturing method, slots may be cut from the tubular sheath using a mill. The driver 112, secured to the flexible rod 110, may be inserted and positioned in the nail 100. Then anchors 108, which may also be made using a mill, are inserted into the slots in the nail 100. These anchors 108 may be secured by pins (not shown) that go through spaces 208 in the anchors 108 or by a ring 210. If a ring 210 is used, the ring 210 may be flexible enough to allow for bending while inserting into the nail 100, but resilient enough that it regains its shape when in position in the nail 100.

In an alternative manufacturing process, the nail 100 may be produced by methods currently known in the art, for example casting. Before cooling, the flexible rod 110 and driver 112 are inserted into the hollow portion of the nail 100. Also, before cooling, the nail 100 is laser etched with tabs outlining the desired structure of the anchors 108. Then the profile of the anchors 108 is stamped into the tabs using a mandrel. This may create a living hinge for the anchors 108. A mandrel may also be used to stamp a rib into the wall of the nail 100. This rib would allow for the placement of a flexible ring 210 if the anchors 108 are held in place by a ring 210. Lastly, one may manufacture the nail 100 by fabricating the dynamic portion of the nail containing the anchors 208 separately then subsequently enjoining the dynamic portion with the remainder of the nail. For example, such enjoining may be accomplished by welding, threading an end of the dynamic portion and the remainder of the nail and screwing them together thereby engendering a connection of the two portions, or other such means providing comparable structural integrity.

What is claimed is:

1. A device for the implantation into osseous material to facilitate healing, comprising:
   an elongated tubular body wherein the elongated tubular body contains;
   a) a mobile elongated rod;
   b) an anchoring element attached to the elongated tubular body that exits through the elongated tubular body at an angle substantially perpendicular to the elongated tubular body and enters a surrounding osseous material at an angle at which the long axis of the anchor is substantially perpendicular to the surface of the osseous material; and
   c) a driver attached to the elongated rod.

2. The device of claim 1 wherein the anchoring element is attached to the elongated tubular body by a hinge.

3. The device of claim 2 wherein the hinge is a living hinge.

4. The device of claim 1 wherein the anchoring element is attached to the elongated tubular body by a pin.

5. The device of claim 1 wherein the anchoring element is attached to the elongated tubular body by a wire.

6. The device of claim 1 wherein the anchor swings longitudinally to the elongated tubular body.

7. The device of claim 1 wherein
   a) the elongated rod is threaded;
   b) the driver is internally threaded; and
   c) the driver moves longitudinally respective to the elongated tubular body when the mobile elongated rod rotates.

8. The device of claim 1 wherein the driver is affixed to the mobile elongated rod and moves in unison with the mobile elongated rod.

9. The device of claim 1 wherein the driver moves within the elongated tubular body and engages the anchoring element thereby causing the anchoring element to exit through the elongated tubular body and engage the surrounding osseous material.

10. The device of claim 9 wherein the driver remains engaged with the anchoring element.

11. The device of claim 10 wherein continued engagement of the driver with the anchoring element holds the anchoring element and driver in position.

12. The device of claim 9, wherein the driver engages the anchoring element by rotating with the mobile elongated rod.

13. The device of claim 9, wherein the mobile elongated rod moves longitudinally within the elongated tubular body and causes the driver to move longitudinally and engage the anchoring element.

14. A device for the implantation into compromised osseous material comprising:
   an elongated tubular body wherein the elongated tubular body contains:
   a) a mobile elongated rod;
   b) an anchoring element attached to the elongated tubular body; and
   c) a driver attached to the mobile elongated rod wherein
      i) the driver moves within the elongated tubular body and engages the anchoring element causing the anchoring element to exit through the elongated tubular body at an angle substantially perpendicular to the elongated tubular body and to extend out of the elongated tubular body to engage the surrounding material such that the long axis of the anchoring element is substantially perpendicular to the surface of the osseous material; and
      ii) the driver remains engaged with the anchoring element holding the anchoring element in position until the driver is moved a second time.

15. The device of claim 14, wherein the driver causes the anchoring element to disengage the surrounding material when the driver is moved the second time.

16. A method for facilitating the healing of damaged osseous material comprising:
   a) inserting an elongated tubular body into the osseous material wherein the elongated tubular body contains a mobile elongated rod attached to a driver within the elongated tubular body;
   b) moving the mobile elongated rod within the elongated tubular body thereby causing the driver to engage an anchoring element attached to the elongated tubular body causing the anchoring element to exit the elongated tubular body at an angle substantially perpendicular to the elongated tubular body; and
   c) causing the anchoring element to engage a surrounding osseous material such that the long axis of the anchoring element is substantially perpendicular to the surface of the osseous material and hold the tubular body in place.

17. The method of claim 16, wherein moving the driver a second time causes the anchoring element to disengage the surrounding osseous material.

18. The method of claim 17 in which the driver is pulled by a handheld power device.

19. The method of claim 16 in which the driver is pulled by a handheld power device.

* * * * *